(12) United States Patent
Reshetnyak et al.

(10) Patent No.: US 8,076,451 B2
(45) Date of Patent: Dec. 13, 2011

(54) SELECTIVE DELIVERY OF MOLECULES INTO CELLS OR MARKING OF CELLS IN DISEASED TISSUE REGIONS USING ENVIRONMENTALLY SENSITIVE TRANSMEMBRANE PEPTIDE

(75) Inventors: Yana K. Reshetnyak, South Kingstown, RI (US); Oleg A. Andreev, South Kingstown, RI (US); Ursula Lehnert, Richmond (GB); Donald M. Engelman, New Haven, CT (US)

(73) Assignees: Board of Governors for Higher Education, State of Rhode Island and Providence Plantations, Providence, RI (US); Yale University, New Haven, CT (US)

( * ) Notice: Subject to any disclaimer, the term of this patent is extended or adjusted under 35 U.S.C. 154(b) by 86 days.

(21) Appl. No.: 11/778,323

(22) Filed: Jul. 16, 2007

(65) Prior Publication Data
US 2008/0233107 A1 Sep. 25, 2008

Related U.S. Application Data

(63) Continuation of application No. PCT/US2006/001895, filed on Jan. 18, 2006.

(60) Provisional application No. 60/752,238, filed on Dec. 20, 2005, provisional application No. 60/644,654, filed on Jan. 18, 2005.

(51) Int. Cl.
*C07K 14/00* (2006.01)
(52) U.S. Cl. .................. 530/324; 514/21.3
(58) Field of Classification Search .......... 530/324; 514/21.3
See application file for complete search history.

(56) References Cited

U.S. PATENT DOCUMENTS
5,739,273 A 4/1998 Engelman et al.

FOREIGN PATENT DOCUMENTS
WO 03106491 A 12/2003

*Primary Examiner* — David Lukton
(74) *Attorney, Agent, or Firm* — Mintz Levin Cohn Ferris Glovsky and Popeo, P.C.; Ingrid A. Beattie

(57) ABSTRACT

A polypeptide with a predominantly hydrophobic sequence long enough to span a membrane lipid bilayer as a transmembrane helix (TM) and comprising one or more dissociable groups inserts across a membrane spontaneously in a pH-dependant fashion placing one terminus inside cell. The polypeptide conjugated with various functional moieties delivers and accumulates them at cell membrane with low extracellular pH. The functional moiety conjugated with polypeptide terminus placed inside cell are translocated through the cell membrane in cytosol. The peptide and its variants or non-peptide analogs can be used to deliver therapeutic, prophylactic, diagnostic, imaging, gene regulation, cell regulation, or immunologic agents to or inside of cells in vitro or in vivo in tissue at low extracellular pH. The claimed method provides a new approach for diagnostic and treatment diseases with naturally occurred (or artificially created) low pH extracellular environment such as tumors, infarction, stroke, atherosclerosis, inflammation, infection, or trauma. The method allows to translocate cell impermeable molecules (peptides, toxins, drugs, inhibitors, nucleic acids, peptide nucleic acids, imaging probes) into cells at low pH. The method allows to attach to the cell surface a variety of functional moieties and particles including peptides, polysaccharides, virus, antigens, liposomes and nanoparticles made of any materials.

17 Claims, 14 Drawing Sheets

Ⓐ — molecule conjugated to the flanking sequence of the pHLIP, which is placed inside cell ($FS_{in}$)

▬ — cleavable link

Ⓑ — molecule conjugated to the flanking sequence of the pHLIP, which stays outside ($FS_{out}$)

SELECTIVE DELIVERY OF MOLECULES INTO CELLS OR MARKING OF CELLS IN DISEASED TISSUE REGIONS USING ENVIRONMENTALLY SENSITIVE TRANSMEMBRANE PEPTIDE

PRIORITY INFORMATION

This application claims the benefit of International Patent Application Serial No. PCT/US06/07881 filed on Jan. 18, 2006, which claims priority to U.S. Provisional Patent Application Ser. No. 60/752,238 filed on Dec. 20, 2005 and U.S. Provisional Patent Application Ser. No. 60/644,654 filed on Jan. 18, 2005, all of which are incorporated herein by reference in their entirety.

GOVERNMENT SPONSORSHIP

The United States government has rights in this invention by virtue of grant numbers GM 054160 from the National Institute of Health and 9905671 from the National Science Foundation.

BACKGROUND OF THE INVENTION

1. Field of the Invention

The present invention relates to the field of protein biochemistry, membrane biophysics, specific drug delivery, gene regulation, imaging and diagnostic of diseased tissue. More particularly the invention relates to use of transmembrane polypeptide to target cells and tissue with acidic environment.

2. Description of the Prior Art

Therapeutic and diagnostic compounds must be delivered to the diseased tissue and accumulated there in concentrations suitable for therapeutic or diagnostic purposes. The specific delivery of therapeutic and diagnostic compounds to diseased tissue significantly improves efficacy of treatment or diagnostic accuracy, and dramatically reduces the side effects. Hypoxia and acidosis are physiological markers of many diseased processes such as tumor, atherosclerotic lesions, ischemia, stroke, inflammation, or trauma (Stubbs et al., 2000, Mol. Med. Today, 6, 15; Helmlinger et al., 2002, Clin. Cancer Res. 8, 1284; Izumi et al. 2003, Cancer Treat. Reviews. 29, 541; Leake 1997, Atherosclerosis, 129, 149; Avkiran, 2003, J Card Surg., 18, 3). pH-selective delivery of molecules to the diseased tissue is a further object of the present invention.

In the majority of cases, therapeutic and diagnostic compounds must be translocated into a cell through the cell membrane in order to reach their targets. Many research reagents for the investigation of cellular processes and gene regulation also need to be translocated into cells. The plasma membrane, which is composed mainly of phospholipids and proteins, is a natural barrier for the free diffusion of molecules across it.

Transmembrane functions are mediated by membrane proteins. The folding and insertion of large membrane protein domains into membranes normally requires the active participation of complex translocation machines (van den Berg et al., 4004, Nature 427, 36; Osborne et al., 2005, Annu Rev. Cell. Dev. Biol. 21, 529; White and von Heijne, 2005, Curr. Opin. Struct. Biol. 15, 378), while the insertion and folding of short (<50-60 residues) protein sequences can occur spontaneously (von Heijne, 1994, FEBS Lett. 346, 69; Whitley et al., 1994 EMBO J. 13, 4653; Wimley and White, 2000, Biochemistry 39, 4432; Popot and Engelman, 1990, Biochemistry 29, 4031), releasing energy and translocating one end of the polypeptide into the cell. In recent work, some cases of apparent spontaneous insertion have been shown to require a membrane protein, YidC (see Dalbey and Kuhn for review (J. Cell Biol. 166:769, 2004).

Previously it was reported that a polypeptide derived from the bacteriorhodopsin C helix, consisting of the transmembrane sequence and two flanking sequences, is soluble in aqueous solution and spontaneously inserts across lipid bilayers forming a stable alpha-helix at low pH (Engelman and Hunt, 1998, U.S. Pat. No. 5,739,273; Hunt et al., 1997, Biochemistry, 36, 15177). The peptide does not exhibit any elements of helical secondary structure in solution or on the membrane at neutral pH. Since the peptide inserts into pure lipid vesicles, it cannot require YidC. pH-selective translocation of molecules through the cell membrane is a further object of the present invention.

SUMMARY OF THE INVENTION

A water-soluble polypeptide pHLIP (pH Low Insertion Peptide) with a predominantly hydrophobic sequence long enough to span a membrane lipid bilayer as a transmembrane helix and two flanking sequences (FS) comprising one or more dissociable groups inserts across a membrane spontaneously in a pH-dependant fashion moving one of the FS regions ($FS_{in}$) across the membrane into the cytoplasm and leaving the other ($FS_{out}$) exposed to the aqueous environment outside the cell.

At low extracellular pH, the pHLIP can translocate certain functional moieties conjugated to the $FS_{in}$ part of the polypeptide across the membrane. If the functional moieties are bound to the pHLIP by interactions that are labile in the environment of the cytoplasm, such as disulfide linkages, the functional moiety can be released into the cytoplasm. Examples of molecules that can be translocated and released include Phalloidin, Peptide Nucleic Acids (PNAs), and Dansyl dye.

The pHLIP can anchor a functional moiety conjugated to the $FS_{out}$ part of the polypeptide to a cell membrane at low pH, locating it at the outer surface of a cell. The outer surface location can be useful, for example, to stimulate receptor activities, to image the location of the labeled cell, or to deliver toxic molecules such as diptheria toxin to selectively kill cells in low pH regions.

The pHLIP represents a new technology for fast, selective and efficient delivery of functional moieties into cells in vitro and in vivo.

These and other features of the present invention will now be described in greater detail with reference to the accompanying drawings, wherein:

DETAILED DESCRIPTION OF THE INVENTION

It was previously reported that a polypeptide derived from the bacteriorhodopsin C helix, consisting of the transmembrane sequence and two flanking sequences, is soluble in aqueous solution and spontaneously inserts across lipid bilayers forming a stable alpha-helix at low pH (Engelman and Hunt, 1998, U.S. Pat. No. 5,739,273; Hunt et al., 1997, Biochemistry, 36, 15177). The insertion is driven by protonation of Asp residues located in the transmembrane part of the polypeptide.

Figure 1A:
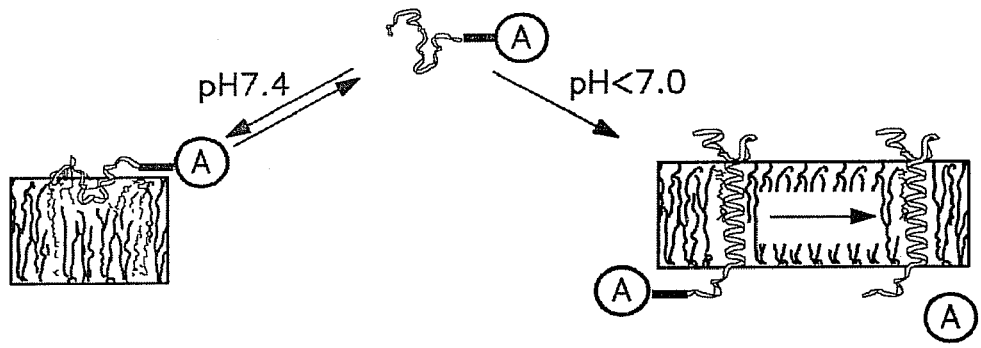
FIG. 1 is a schematic diagram of the delivery of a functional moiety into a cell by pHLIP (a) or anchoring of a functional moiety to the surface of a targeted cell by pHLIP (b)
Figure 1B:
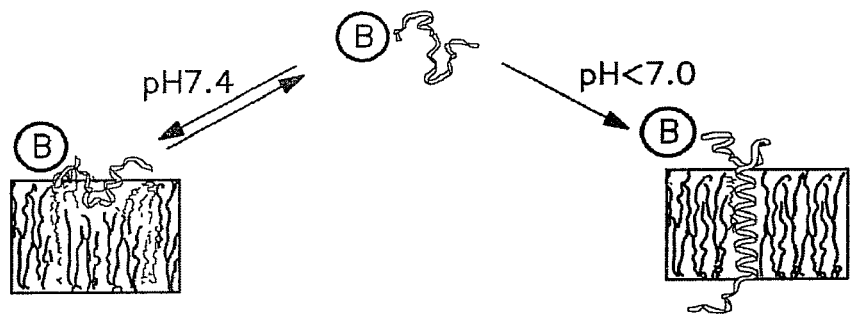

The present invention demonstrates that polypeptide: pHLIP, the sequence: AAEQNPIYWARYADWLFT-TPLLLLDLALLVDADEGTCG (SEQ ID NO: 1) with a predominantly hydrophobic sequence long enough to span a membrane lipid bilayer as a transmembrane helix and comprising one or more dissociable groups which selectively deliver and translocate compounds into cells with low extracellular environment in vitro and in vivo as shown in FIG. 1. FIG. 1 is a schematic diagram of functional moiety delivery into a cell (a) or anchoring of functional moiety to the targeted cell (b). At physiological pH, the peptide-functional moiety conjugate interacts weakly with a membrane. At low pH, the peptide forms a transmembrane helix with one terminus inserted in the cytoplasm. Cleavage of link between peptide and functional moiety releases it inside cell.

Topology of Insertion

To identify the topology of the insertion of the pHLIP, an established assay was used which is based on application of the membrane-impermeable dithionite ion ($S_2O_4^{-2}$) that can chemically modify the NBD fluorophore and quench its fluorescence (Chattopadhyay, 1990, Chem Phys Lipids 53, 1).

Figure 2A:
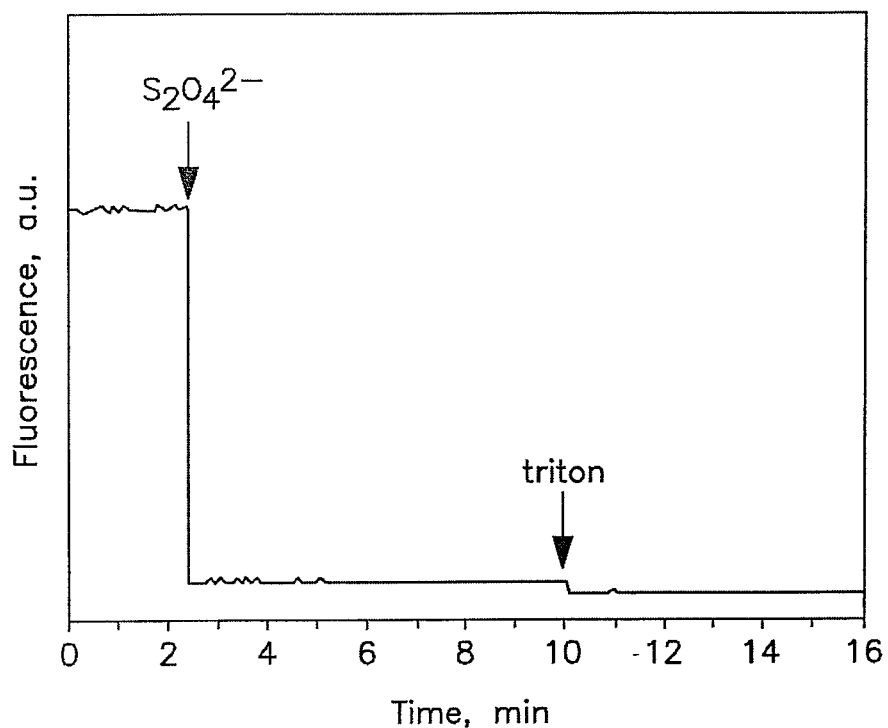
FIGS. 2a and 2b are graphs of time vs. fluorescence intensity wherein in (a) sodium dithionite was added to pHLIP with NBD on FSout, inserted into POPC LUVs and (b) POPC LUVs containing dithionite ion inside were added to the NBD-peptide at pH8.0, then, decreasing the pH triggered insertion of the peptide into liposomes, illustrating the process of labeling cells at low pH.
Figure 2B:
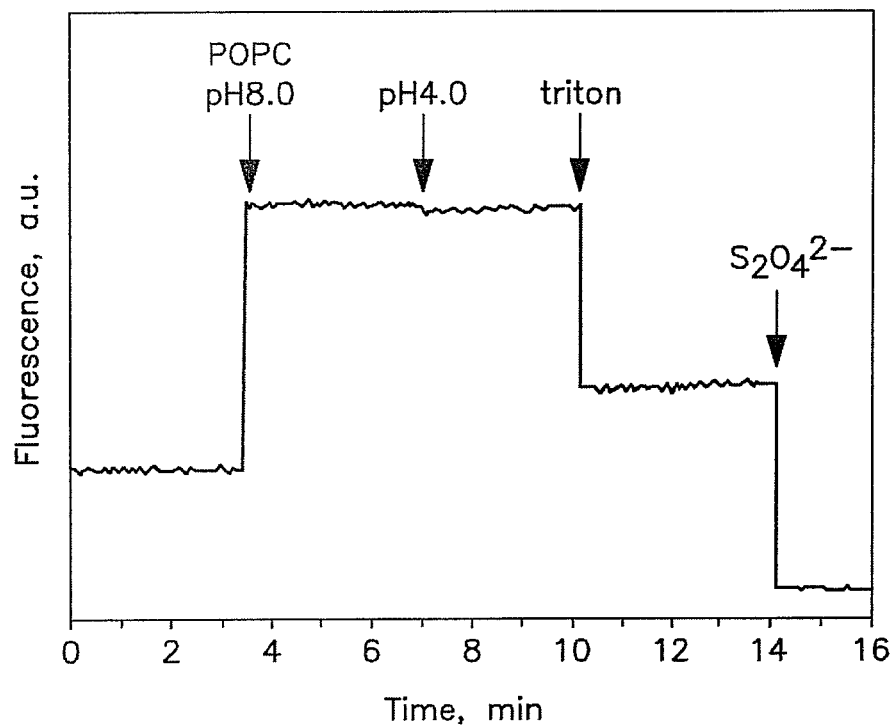
Figure 3A:
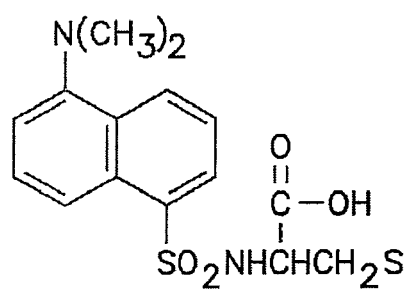
FIG. 3a shows the covalent chemical structure of dansyl dye and FIG. 3b shows fluorescence images of HeLa cells incubated (for 15 min) with a pHLIP-S—S-dansyl cleavable construct (7 μM) at pH 5.5, 6.5, 7.0 and 7.4 and washed with PBS buffer at pH7.4, where the S—S linkage is to FSin, and the dye is released into cells in a pH-dependant fashion.
Figure 3B:
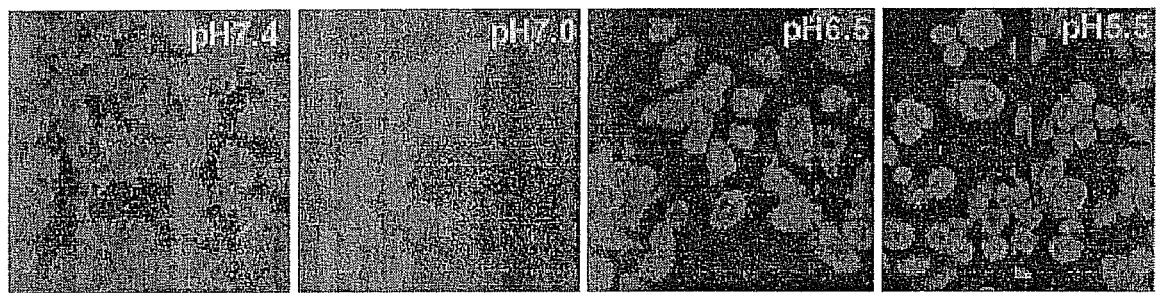

Labeled pHLIP was inserted into POPC liposomes. The topology of the pHLIP in a lipid bilayer was determined using the NBD-dithionite quenching reaction. The fluorescence signal of NBD attached to the N-terminus of peptide was monitored at 530 nm when excited at 470 nm. The maximum position of the NBD fluorescence spectrum of the labeled peptide inserted into liposomes was 530 nm, which indicates that the NBD fluorophore is surrounded by a polar environment (with dielectric constant ~70, for comparison, the maximum position of the NBD-PE spectrum, where the NBD is located at the level of phosphate group, is 522 nm). Addition of the dithionite ion led to the complete quenching of NBD fluorescence (FIG. 2a). A second population of liposomes with dithionite trapped inside them was mixed with the labeled peptide at neutral pH and then the pH was lowered to trigger peptide insertion. No change in fluorescence signal was detected (FIG. 2b), showing that dithionite trapped in the liposomes did not react with NBD, showing that the N-terminus of the peptide is located outside of the liposome and that the peptide does not induce membrane leakage of dithionite. In (FIG. 2a) sodium dithionite was added to the NBD-peptide inserted into POPC LUVs. In (FIG. 2b) POPC LUVs containing dithionite ion inside were added to the NBD-peptide at pH8.0, then, decreasing the pH triggered insertion of the peptide in liposomes. Triton was used for the disruption of liposomes. The concentration of the peptide used in the experiments was 7 µM. NBD quenching was observed after disruption of the membrane by Triton. These data demonstrate that at low pH the N-terminus is localized outside and, consequently, the C-terminus is located inside of the POPC liposomes.

pH-Dependent Translocation of Molecule Through Cell Membrane pHLIP conjugated via a disulfide bond to dansyl dye (FIG. 3a) was tested for delivery of the dye into live HeLa cells at different pHs (FIG. 3b). The cells were incubated with the fluorescently-labeled peptide for 15 min at pH 5.5, 6.5, 7.0 or 7.4 and then washed at pH 7.4 to remove any reversibly bound peptide. The uptake of dansyl was significantly higher at low pH. The relative uptakes were 18%, 48%, 78% and 100% at pH7.4, 7.0, 6.5 and pH5.5, respectively. Dansyl alone does not penetrate cells.

Translocation of Molecule and Release it Inside Cell at Low pH

Figure 4A:
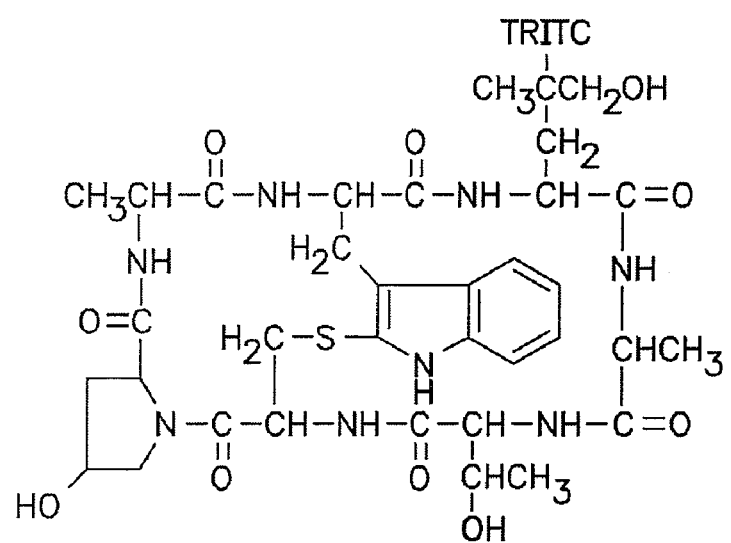
FIG. 4a shows the covalent chemical structure of phalloidin and FIG. 4b shows fluorescence images of HeLa cells incubated (for 15 min) with a pHLIP-S—S-Phalloidin-TRITC cleavable construct (4 µM) at pH 7.4 (left) and 6.5 (right), where the phalloidin is attached to FSin and is released into the cytoplasm upon insertion and subsequent disulfide bond reduction.
Figure 4B:
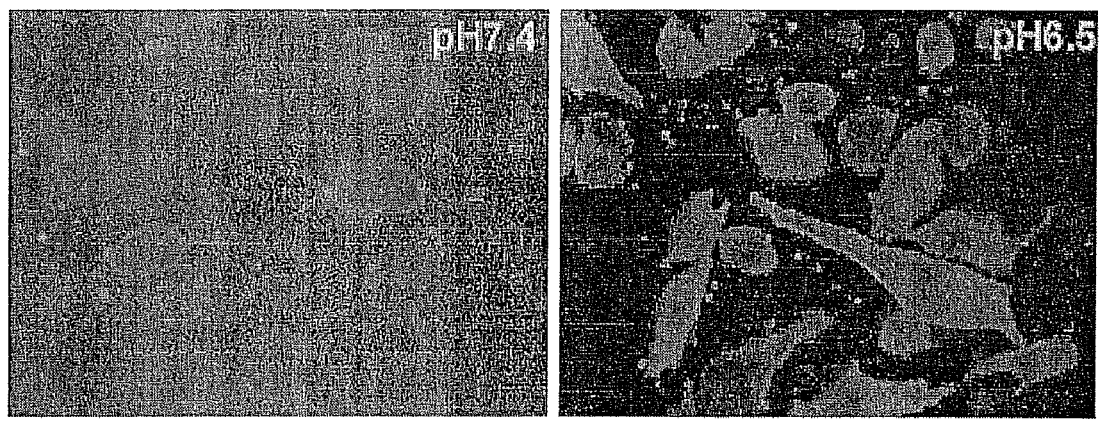

To test the ability of pHLIP to translocate peptides across the cell membrane a water soluble cyclic peptide, phalloidin, from the *Amanita phalloides* mushroom was chosen. Phalloidin binds tightly to actin filaments at nanomolar concentration and strongly inhibits their depolymerization (Weiland et al., 1977, Curr. Probl. Clin. Biochem., 7, 11; Wehland et al., 1977, Proc. Natl. Acad. Sci. U.S.A, 74, 5613), but does not normally affect cells since it is too polar to cross a membrane. Fluorescent phalloidin is commonly used to label actin filaments in permealized cells. Actin filaments stained with fluorescent phalloidin have an easily recognizable filamentous pattern, which cannot be mistaken for the other cellular structures, organelles or membrane staining. Therefore the delivery of fluorescent phalloidin by pHLIP into live cells can easily be verified by fluorescence microscopy. Fluorescently labeled phalloidin (Phalloidin-TRITC) via an S—S bond to the C-terminus of pHLIP was conjugated using a bifunctional cross-linker. Cells were incubated with a pHLIP-S—S-Phalloidin-TRITC cleavable construct at different pHs and subsequently washed with cell culture medium solution, pH 7.4. Penetration of the C terminus into the reducing environment of the cytoplasm was expected to cleave the S—S bond and release Phalloidin-TRITC. Bright fluorescent staining of actin filaments was observed at low pH, while at physiological pH some fluorescent staining of membranes but not of the cytoskeleton was observed (FIG. 4). The treatment of cells with Phalloidin-TRITC or crosslinker-Phalloidin-TRITC in the presence or absence of peptide did not give fluorescent staining of actin filaments at pH 6.0-7.4. The fluorescence was extremely weak after pH 7.4 incubation and localized to the plasma membrane. Strong fluorescence of actin filaments was observed after pH 6.5 incubation.

Quantification of Uptake

FACS were used to quantify the pH-dependent translocation of fluorescent phalloidin by the peptide through the membranes of HeLa cells in suspension. As shown in FIG. 5, translocation of fluorescent phalloidin is pH-dependent and does not involve endocytosis. Cytofluorometry of HeLa cells treated (for 1 hour) with (6 µM) pHLIP-S—S-Phalloidin-TRITC cleavable construct at pH7.4, T=37° C. (b), pH6.5, T=37° C. (c) and pH6.5, T=4° C. (d). The untreated cells are shown (a). Cells treated with pHLIP-S—S-Phalloidin-TRITC at pH7.4 exhibited a very low level of fluorescence. However, at low pH a population of highly fluorescent cells was observed. The efficiency of delivery at 4° C. was the same as at 37° C., showing that endocytosis is not involved in the uptake mechanism.

Figure 5A:
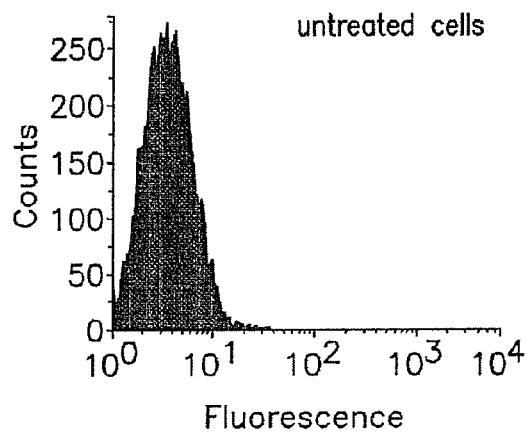
FIGS. 5a-5d are graphs of fluorescence vs. counts of untreated cells and cells treated in suspension (for 1 hour) with a pHLIP-S—S-Phalloidin-TRITC cleavable construct (6 µM) at various pH's and temperatures, showing the labeling of cells in a pH dependant fashion that is not inhibited by low temperature (4 deg. C.).
Figure 5C:
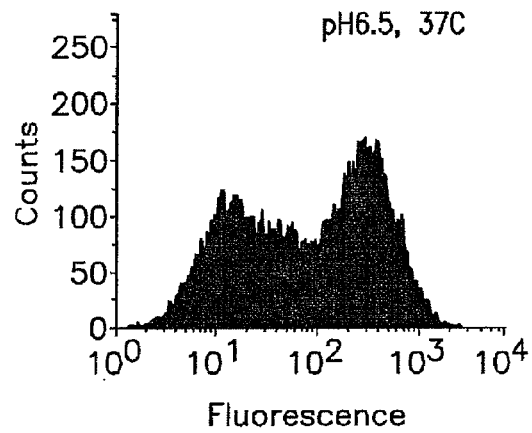
Figure 5B:
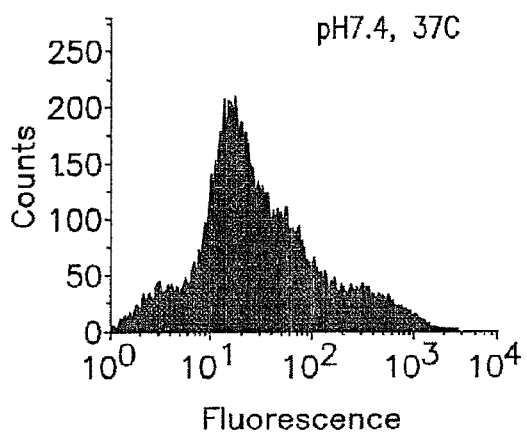
Figure 5D:
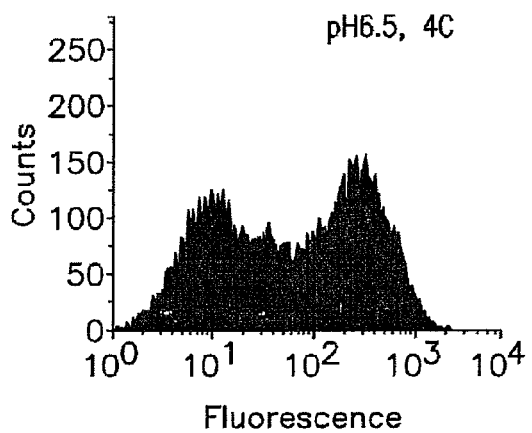

Cells treated with pHLIP-S—S-Phalloidin-TRITC exhibited a very low level of fluorescence due too limited membrane attachment at pH7.4. However, at low pH a population of highly fluorescent cells was observed (FIG. 5c). The efficiency of Phalloidin-TRITC delivery by pHLIP into cells at low temperature was the same as at 37° C. (FIG. 5d), providing the additional evidence that the mechanism of translocation is not by endocytosis. The appearance of discrete populations of fluorescent cells might reflect a difference in the delivery of Phalloidin-TRITC from variation of cytoplasmic reducing power in cells in different phases of the cell cycle (Conour, 2004, Physiol Genomics, 18, 196) and removal with the peptide during cell washing at pH 7.4, since the insertion of the peptide is reversible. The release of Phalloidin-TRITC inside the cell depends on the glutathione concentration, which is known to vary significantly during the cell cycle, reaching a maximum at G2/M and a minimum at G1 (Conour, 2004, Physiol Genomics, 18, 196). Since the incubation time (1 hour) is much less than the HeLa cell cycle time (18 hours), the cells that happen to be in G2/M might take up more phalloidin than the rest. Long incubations of cells with peptide-phalloidin have been avoided to minimize cell exposure to low pH, especially at low temperature.

Mechanism of Molecules Translocation Through the Membrane by pHLIP

Figure 6A:
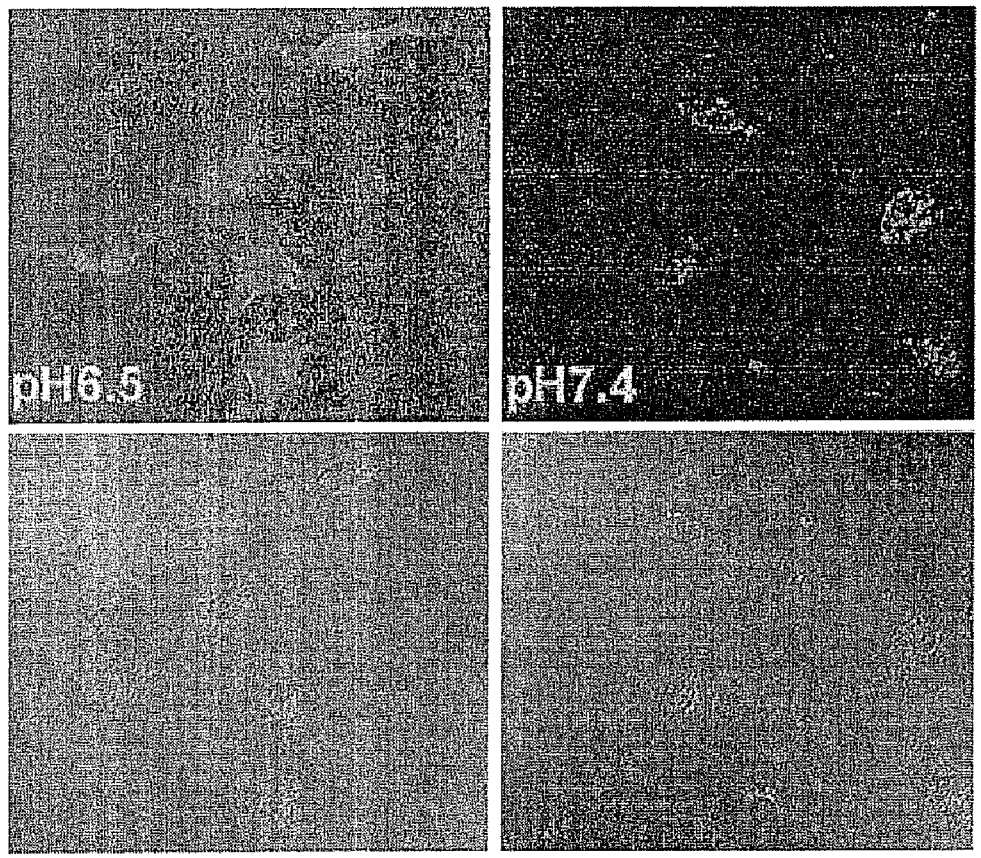
FIG. 6a shows fluorescence and bright field confocal images of JC breast adenocarcinoma cells incubated (for 1 hour) with 1 µM of a pHLIP-Phalloidin-TRITC non-cleavable construct having the Phalloidin-TRITC on FSin at pH 6.5 (right)
Figure 6B:
FIG. 6b is of fluorescence images of JC breast adenocarcinoma cells incubated with the same pHLIP-Phalloidin-TRITC non-cleavable construct at pH 6.5 at different magnification (40× and 100×)

To demonstrate that the peptide itself does not enter the cell, the fact (reported previously, Hunt et al., 1997, Biochemistry, 36, 15177) that a pH increase leads to the reversal of insertion and the release of the peptide from lipid bilayers was exploited. Phalloidin-TRITC was conjugated to the C-terminus of the peptide via a non-cleavable covalent bond, incubated with cells at pH 6.5 and washed with PBS buffer at the same pH (FIG. 6a, left, incubated for 1 hour with the non-cleavable pHLIP-Phalloidin-TRITC construct 1 µM at pH 6.5 right). FIG. 6b is of fluorescence images of JC breast adenocarcinoma cells incubated with the non-cleavable pHLIP-Phalloidin-TRITC construct at pH 6.5 at different magnification (40× and 100×) demonstrate no staining of actin filaments however there was staining of the plasma membrane. Then, cells were washed with the buffer at pH 7.4, resulting in the removal of the peptide together with Phalloidin-TRITC, and just traces of fluorescence were observed (FIG. 6a). These procedures were repeated with the peptide conjugated to Texas Red and Rhodomine (data not shown), with similar results. The experiments demonstrate again that the translocation mechanism does not involve the endocytic pathway, since the pHLIP stays attached to the cell membrane at low pH and can be washed out at neutral pH.

Figure 7A:
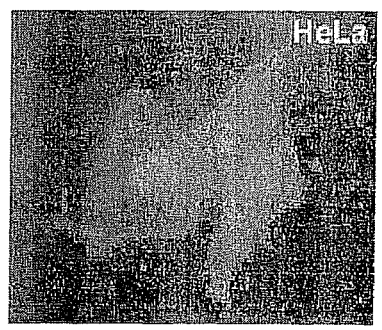
FIGS. 7a-7c are images of HeLa, breast JC and prostate TRAMP-C1 cancer cells with fluorescent actin filaments, demonstrating the transport and release of Phalloidin TRITC into the cytoplasm.
Figure 7B:
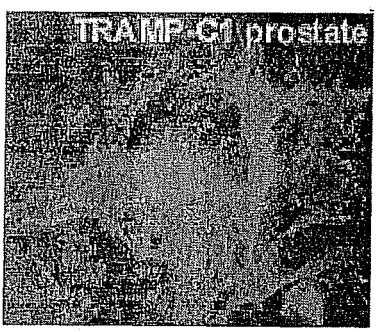
Figure 7C:
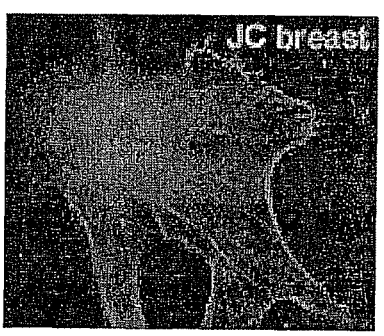

The delivery of phalloidin attached by S—S bond to pHLIP in different cell lines: human HeLa, mouse TRAMP-C1 prostate, and mouse JC breast cancer cells, was also tested. In each case the characteristic staining of actin filaments at pH<7.0 (FIG. 7) wherein cells were incubated for 1 hour with the cleavable pHLIP-S—S-Phalloidin-TRITC (0.5-1 µM) at pH6.5 followed by washing with PBS at pH7.4 was observed. This demonstrated that the translocation of molecules by pHLIP does not depend on the presence of receptors on particular types of cells.

Cytotoxicity and Membrane Leakage Test

Figure 8A:
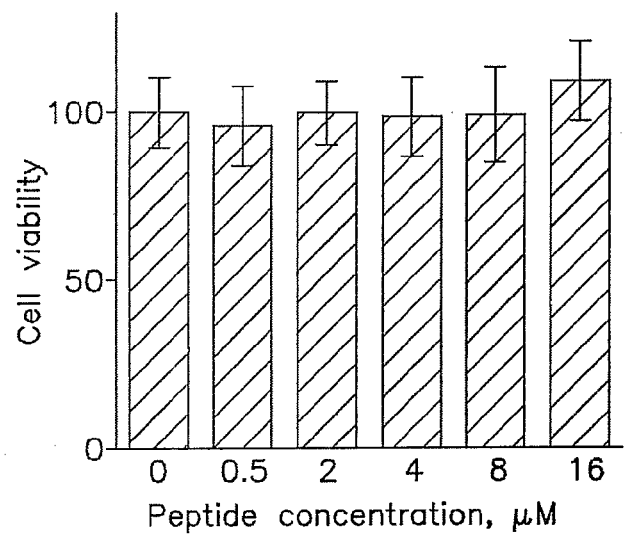
FIG. 8a are bar graphs of peptide concentration vs. cell viability
Figure 8B:
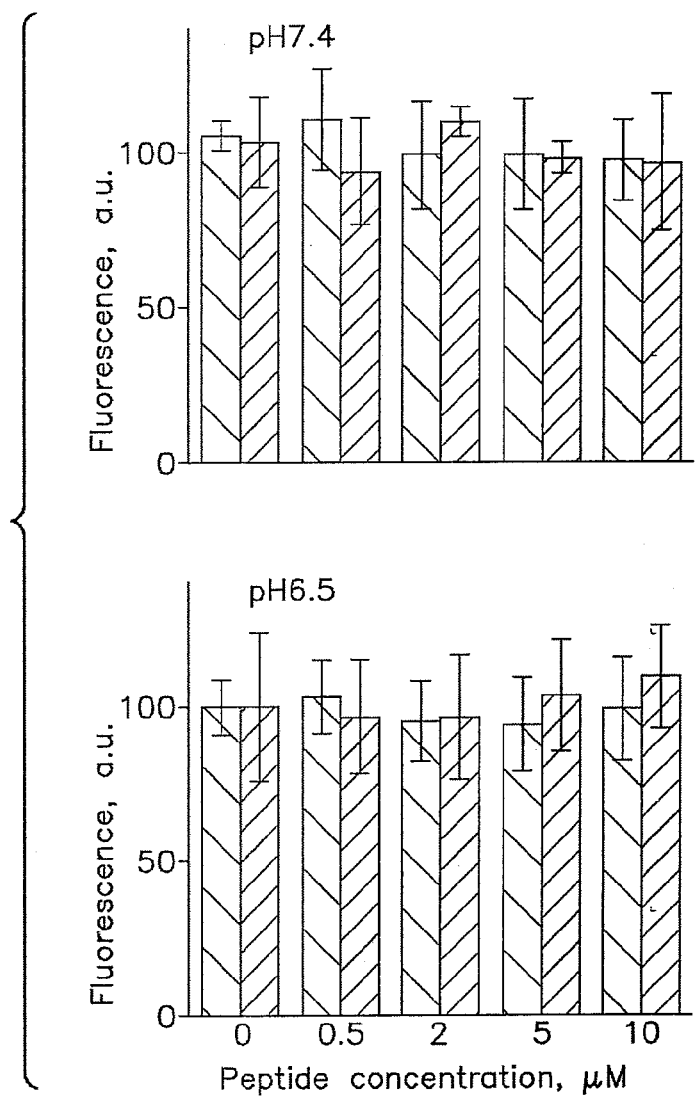
FIG. 8b is a bar graph of peptide concentration treated with cells vs. fluorescence of membrane-impermeable agents: nuclear-staining SYTOX-Orange (0.5 µM) (light columns) and phalloidin-TRITC (2 µM) (dark columns) incubated with peptide-treated cells at two different pH values, untreated cells are taken as 100%, showing that the peptide has minimal cytotoxicity.

The peptide's cytotoxicity and its ability to induce membrane leakage was investigated. As shown in FIGS. 8a and 8b, are the cell toxicity and membrane leakage tests. Incubation of HeLa cells with the peptide at concentrations up to 16 µM for 24 hrs under physiological conditions does not affect cell viability (FIG. 8a). Membrane leakage was tested by incubation of HeLa cells at various concentrations of peptide (up to 10 µM) at pH 7.4 and 6.5 for 1 hr, followed by the addition of cell-impermeable agents: Phalloidin-TRITC and nuclear-staining SYTOX-Orange. We observed no increase in uptake of Phalloidin-TRITC or SYTOX-Orange in the cells treated with peptide at either pH 6.5 or 7.4 (FIG. 8b). The uptake of Phalloidin-TRITC or SYTOX-Orange was 10 times less than the uptake in cells treated with triton, which used for cell membrane permeabilization. So, as in the case of liposomes, the peptide did not induce pore formation.

Toxicity Study

Preliminary toxicity study was carried out. 100 µl of 150 µM of peptide was given as a single injection in vein tail to 4 female C3D2F1 and 4 male C57/Bl mice. The final concentration was 4 mg/kg. Mice were observed by a veterinarian the day after an injection and during the next 6 weeks. No physiological and behavioral changes were observed in all of the mice.

The Accumulation of the pHLIP in Tumor In Vivo

Figure 9:
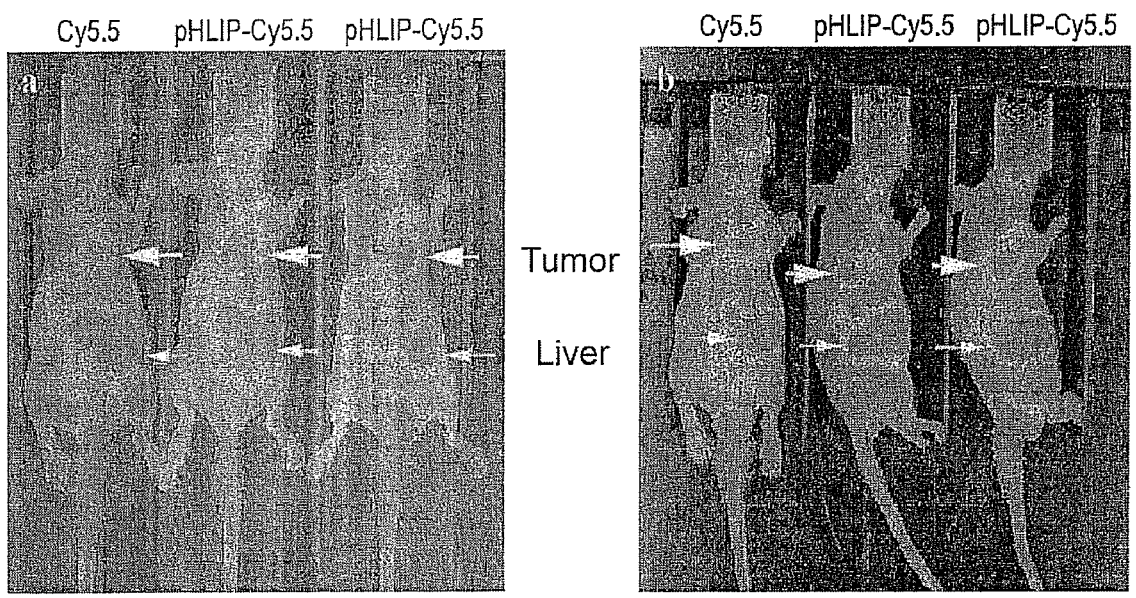
FIG. 9 shows whole-body fluorescent images of athymic female nude mice bearing tumors 3 mm in size 4 hours (a) and 24 hours (b) after the injection of 100 µl of 50 µM Cy5.5 alone and Cy5.5 covalently attached to the Cys residue on N-terminus of the pHLIP, showing that the peptide locates in the tumor.
Figure 10:
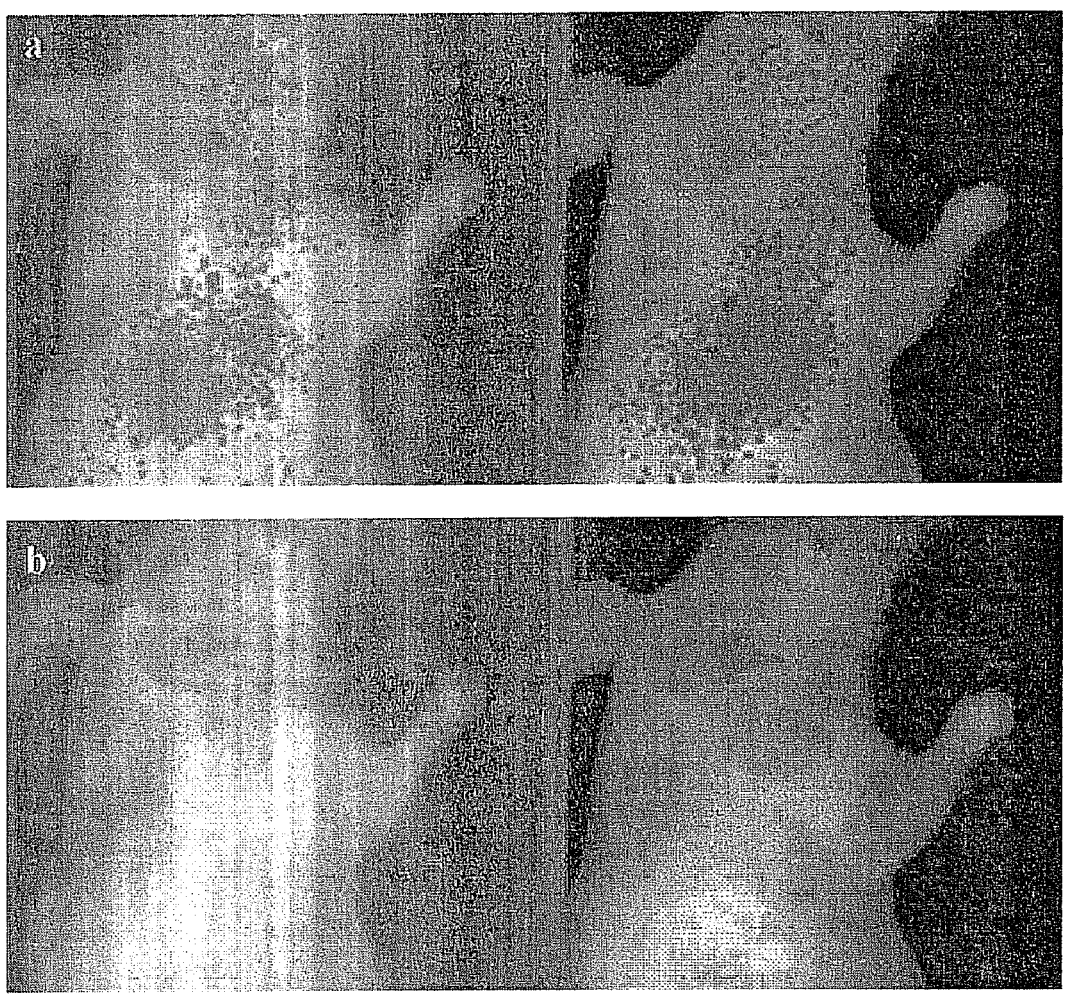
FIG. 10 shows whole-body fluorescent images of athymic female nude mice bearing 3 mm tumors 24 hours after the injection of 100 µl of 50 µM Cy5.5-pHLIP (1 mg/kg)

To study the pHLIP distribution in vivo, covalently attached to the pHLIP near infrared fluorescent dye Cy5.5 was injected into mice bearing tumor and performed whole-body fluorescence imaging. Human tumor MDA-MB-231 was originated by injection of tumor cells ($2\times10^7$ cells/flank/0.2 ml) in the right flank of adult athymic female nude mice. When the tumor reached the size of 3 mm in diameter, 100 μl of 50 μM of Cy5.5 alone or Cy5.5 covalently attached to the pHLIP was given as a single injection into vein tail. The imaging was performed immediately, after 1, 2, 4 hour and next day after 24 hours (FIGS. 9 and 10). The dye and peptide-dye accumulated in liver and kidney, the organs, which usually readily absorb any compounds. The ratios of (liver+kidney)/tumor were 5.9 and 3.6 in mice to which dye alone and pHLIP-dye were injected accumulation for mice. The images clearly show that peptide-dye accumulated in tumor at concentration that is enough to perform imaging (FIG. 10). The accumulation of pHLIP-Cy5.5 in tumor was in 1.6 times higher than accumulation of dye alone. The ration of (liver+kidney)/tumor was 1.6 and 2.6 for pHLIP-Cy5.5 and Cy5.5 alone, respectively. It suggests that contrast of tumor was much better with peptide.

Methods

Synthesis of Peptide and Peptide-cargo Constructs pHLIP was prepared by solid-phase peptide synthesis using standard Fmoc (9-fluorenylmethyloxycarbonyl) chemistry and purified by reverse phase chromatography (on C18 column) at the W. M. Keck Foundation Biotechnology Resource Laboratory at Yale University. In a typical preparation of the soluble form of the peptide, the lyophilized powder was dissolved in a solution containing 6 M urea and was transferred to working buffer by using a G-10 size-exclusion spin column. The concentration of the peptide was determined by absorbance ($\epsilon_{280}=13940$ $M^{-1}$ $cm^{-1}$) and was confirmed by quantitative amino acid analysis. The peptide was labeled at its single C-terminal cysteine residue with dansyl, TexasRed or Rhodamine by incubation with didansyl (Sigma), TexasRed maleimide (Molecular Probes) or tetramethylrhodamine maleimide (Molecular Probes) in 10 mM Tris-HCl, 20 mM NaCl, 6M urea, pH8.0 in dark at 4° C. for 24 h. The conjugated peptides were purified on a G-10 size-exclusion column and transferred to PBS buffer, pH 7.4. The concentration of labeled peptide was determined by absorbance (Dansyl: $\epsilon_{340}=4300$ $M^{-1}$ $cm^{-1}$, TexasRed: $\epsilon_{582}=112000$ $M^{-1}$ $cm^{-1}$, Rhodamine: $\epsilon_{542}=65000$ $M^{-1}$ $cm^{-1}$).

pHLIP was conjugated to phalloidin-rhodamine (Phalloidin-TRITC) (Sigma) using bi-functional photocrosslinkers: S-[2-(4-Azidosalicylamido)ethylthio]-2-thiopyridine (AET, Molecular Probes) or benzophenone-4-iodoacetamide (Molecular Probes). The first crosslinker (AET) makes an S—S bond with the C-terminus of the peptide and binds to Ph-TRITC under UV irradiation (pHLIP-S—S-Phalloidin-TRITC). The second crosslinker was used for the synthesis of the non-cleavable construct (pHLIP-Phalloidin-TRITC). pHLIP was incubated with the crosslinker in PBS in the dark at 4° C. for 24 h. Excess crosslinker was removed using a G-10 size-exclusion spin column. 5× molar excess of Phalloidin-TRITC was added to the pHLIP-crosslinker and illuminated at 340 nm for 30 min. The unreacted Phalloidin-TRITC was removed using a G-10 size-exclusion column. The concentration of rhodomine was determined by absorption at 542 nm ($\epsilon_{542}=65000$ $M^{-1}$ $cm^{-1}$). Separately, the Phalloidin-TRITC was conjugated to AET without peptide. The conjugation of Phalloidin-TRITC to cross-linker or pHLIP did not affect its ability to bind to F-actin (data are not shown).

TAMRA-o-o-CATAGTATAAGT-o-Cys-NH2 (SEQ ID NO: 2) peptide nucleic acid with Cys and fluorescent dye, TAMRA, was synthesized by Applied Biosystems, MA. This PNA targets MDM2 mRNA (Shiraishi, and Nielsen, 2004, Nucleic Acids Res., 32, 4893). PNA-TAMRA was incubated with 4 times molar excess of pHLIP for 24 hrs in PBS pH 7.4, 4° C. pHLIP-S—S-PNA-TAMRA construct was purified on G-10 column. Concentration was determined by measuring absorption at 546 nm ($\epsilon_{542}=65000$ $M^{-1}$ $cm^{-1}$).

Liposome Preparation

Large unilamellar vesicles (LUVs) were prepared by sonication. The POPC (1-Palmitoyl-2-Oleoyl-sn-Glycero-3-Phosphocholine, Avanti Polar Lipids, Inc.) phospholipid was dissolved in chloroform. Following removal of the solvent using a rotary evaporator, the phospholipid film was dried overnight and then rehydrated in 10 mM Tris-HCl, 20 mM NaCl, pH 8.0 and vortexed. The suspension was sonicated using a Branson titanium tip ultrasonicator until the solution become transparent. The liposomes distribution was evaluated by dynamic light scattering. The vesicles radius was 72.6±4.6 nm (polydispersity was 13.6±6.7%). To prepare liposomes with dithionite inside them, the phospholipid film was rehydrated in 1 M Tris buffer, pH 8.0 containing 1 M dithionite. Untrapped dithionite was removed from the solution of liposomes using a dialysis cassette with 10 kDa cut off pores. Dialysis was performed against 10 mM Tris-HCl, 20 mM NaCl, pH 8.0 for 4 hours with hourly solution changes.

Detection of Peptide Topology

External addition of dithionite ($Na_2S_2O_4$) to LUVs chemically quenches the NBD fluorescence in the outer leaflets of the bilayers. The peptide was labeled at N-terminus with NBD by incubation with NBD-Cl (Molecular Probes) in 10 mM Tris-HCl, 20 mM NaCl, pH7.0 in dark at 4° C. for 24 hours (the peptide:NBD ratio was 1:20). The conjugated peptide was purified in a G-10 size-exclusion column. The concentration of labeled peptide was determined by absorbance ($\epsilon_{480}=25000$ $M^{-1}$ $cm^{-1}$, $\epsilon_{336}=9800$ $M^{-1}$ $cm^{-1}$). The labeled peptide was incubated with liposomes at neutral pH and insertion was triggered by the reducing of pH to 4.0. The fluorescence spectra of the peptide labeled with NBD in solution and inserted into lipid bilayer were recorded on a SLM8000 spectrofluorometer. Changes in the fluorescence signal of NBD were monitored at 530 nm (excited at 470 nm) after addition of the dithionite, and following disruption of the liposomes by triton. In other experiments, liposomes containing dithionite were added to the labeled peptide in solution at pH 8.0, the pH was then decreased to 4.0, triton was added to disrupt the liposomes and more dithionite was added for the complete quenching of the NBD fluorescence.

Cell Lines

Both human and mouse cancer cell lines were used in the study. HeLa cells were provided by the Cancer Center of the Yale University Medical School. Prostate, TRAMP-C1 (CRL-2730), and breast adenocarcinoma (CRL-2116) were from the American Type Culture Collection (ATCC). Cells were cultured in Dulbecco's modified Eagle's medium (DMEM) supplemented with 10% fetal bovine serum (FBS), 100 units/ml penicillin, 0.1 mg/ml streptomycin, and 2 mM glutamine in a humidified atmosphere of 5% $CO_2$ and 95% air at 37° C.

Cytotoxicity Assay

Cytotoxicity was tested using a standard colorimetric assay according to an established protocol provided by Promega, Inc. HeLa cells were loaded in the wells of 96 well plates (20,000 cells per well), incubated for 24 hours in DMEM supplemented with 10% FBS, 100 units/ml penicillin, 0.1 mg/ml streptomycin, 2 mM glutamine in a humidified atmosphere of 5% $CO_2$ and 95% air at 37° C. The growth medium was then replaced with the same medium but containing 1% of FBS and increasing amounts of pHLIP (0.5, 1, 2, 4, 8 and 16 µM). After 24 hours of incubation, the solution was replaced with DMEM and a colorimetric reagent (CellTiter 96 $AQ_{ueous}$ One Solution Assay) was added for 1 hour followed by measuring absorbance at 490 nm in the plate-reader. All samples were prepared in triplicate.

Membrane Leakage Assay

HeLa cells were loaded in 96 well plates (2,000 cells per well), incubated for 24 hours in DMEM supplemented with 10% FBS, 100 units/ml penicillin, 0.1 mg/ml streptomycin, 2 mM glutamine in a humidified atmosphere of 5% $CO_2$ and 95% air at 37° C. The growth medium was then replaced with PBS buffer containing 1 mM $CaCl_2$ and 1 mM $MgCl_2$ at pH7.4 or 6.5 and increasing amounts of the peptide (0.5, 2, 5 and 10 µM). After 1 hour, 2 µM of Phalloidin-TRITC and 0.5 µM of SYTOX-Orange (Molecular Probes) were added for 10 min and, then, washed with PBS buffer, pH7.4. The rhodamine fluorescence was measured at 580 nm with excitation at 544 nm by plate-reader. The cell membrane was subsequently disrupted by adding 0.5% Triton-100 and a new portion of the 2 µM of Phalloidin-TRITC and 0.5 µM of SYTOX-Orange followed by washing with PBS. The fluorescence signal was detected before and after washing, respectively. All samples were done in triplicate.

Fluorescence Microscopy

For the fluorescence microscopy studies, the cells were grown in 35 mm dishes with 10 mm glass bottom windows coated with collagen. Cells were washed with PBS buffer containing 1 mM $CaCl_2$ and 1 mM $MgCl_2$ with pH 5.5, 6.5, 7.0 or 7.4 and then incubated in PBS at the experimental pH in the absence or presence of varied concentrations (0.1-7 µM) of the pHLIP-S—S-dansyl, pHLIP-dye (TexasRed or Rhodamine), pHLIP-S—S-Phalloidin-TRITC, pHLIP-Phalloidin-TRITC or pHLIP-S—S-PNA-TAMRA constructs. The medium pH was measured before and after incubation. The time of incubation was varied from 15 to 60 min. The cancer cells can acidify the medium (PBS buffer) in a few minutes if the incubation volume is small, creating the problem of maintaining constant pH 7.4 in the PBS incubation buffer. It was preferred to use a low density of cells in the chamber, a larger volume and a higher phosphate concentration (up to 50 mM instead of the standard 10 mM PBS) and the pH before and after the experiments were routinely checked. The incubation was followed by the replacement of the PBS buffer with Leibovitz's L-15 phenol free medium (supplemented with 5% FBS, 100 units/ml penicillin, 0.1 mg/ml streptomycin, and 2 mM glutamine) at the experimental pH for 1 hr and then (if not indicated otherwise) at pH 7.4. To monitor multinucleated cells nuclear-staining dye DAPI (Sigma-Aldrich) were used. HeLa cells were treated with pHLIP-S—S-Phalloidin-TRITC in PBS at pH6.5 for 1 hour followed by changing solution with DMEM supplemented with 10% FBS, 100 units/ml penicillin, 0.1 mg/ml streptomycin, 2 mM glutamine in a humidified atmosphere of 5% $CO_2$ and 95% air at 37° C. After 48 hours 0.5 µM of DAPI was added followed by washing. Fluorescent images were taken using an inverted epi-fluorescence microscope Olympus IX71. Some images of cells stained with pHLIP-Phalloidin-TRITC non-cleavable construct were taken on the Zeiss Axioplan 2 light microscope with Zeiss LSM 5 PASCAL laser scanning module with excitation at 543 nm of He/Ne laser. The images of cells stained with dansyl were taken on BioRad MRC-1024 two-photon confocal microscope with excitation at 740 nm. Each time fluorescence microscopy experiments were performed and observed the translocation of cargo by pHLIP, it was verified that the labeled cells were alive by using of dead cell marker SYTOX-Green (Molecular Probes).

Flow Cytometry

Analytic flow cytometric measurements were performed using a fluorescence activated cell sorting (FACS) instrument. Ten thousand cells were analyzed in each sample. The cells were suspended in PBS at pH 6.5 or 7.4 in presence and absence of (6 µM) pHLIP-S—S-Phalloidin-TRITC at 40 or 37° C. for 1 hour. Then they were washed twice with PBS buffer pH 7.4, resuspended in PBS pH 7.4, and analyzed on the FACS instrument.

Whole-body Fluorescence Imaging

Human breast adenocarcinoma MDA-MB-231 (HTB-26, ATCC) cells was cultured in Leibovitz's L-15 medium supplemented with 10% fetal bovine serum, 100 units/ml penicillin, 0.1 mg/ml streptomycin, 2 mM glutamine in humidified atmosphere of 5% $CO_2$ and 95% air at 37° C. Human tumor MDA-MB-231 was originated by injection of tumor cells ($2 \times 10^7$ cells/flank/0.2 ml) in the right flank of adult athymic female nude mice. Injection was performed while the animal was under anesthesia using ketamine (90 mg/kg) and xylazine (9 mg/kg) mixture. Nude mice was anesthetized and intravenously injected with the peptide labeled with Cy5.5 dye (1 mg/kg). As a control one mouse was injected with Cy5.5 dye only. The images of mice at several positions were taken 10 min, 30 min, 1, 2, 4 and 24 hrs after injection on Xenogen (Alamedca, Calif.) IVIS imaging system.

Toxicity Study 4 weeks old female and male mice were injected with L-peptide (L-amino acids) or D-peptide (D-amino acids) intravenously at maximum concentration (4 mg/kg) and observed by a veterinarian during 6 weeks. No physiological and behavioral changes were observed in all mice.

EXAMPLE 1

Selective Translocation of Phalloidin Through the Cell Membrane by pHLIP

Microtubules and actin filaments are cytoskeleton proteins polymers critical for cell growth and division, motility, signaling, and the development and maintenance of cell shape. The most important characteristic of the cytoskeleton is its ability to reorganize rapidly and locally in response to stimuli. This is achieved by the non-equilibrium dynamics of the reaction of the polymerization of actin monomers into actin filaments and αβ-tubulin dimers into microtubules. Microfilament actin remodeling is associated with cell proliferation, motility and invasion (Egelman, 1997, Structure 5, 1135; Kodama et al., 2004, J Cell Biol., 167, 203; Rao and Li, 2004, Curr Cancer Drug Targets., 4, 345) and is a critical determinant of cancer metastasis (Banyard and Zetter, 1998, Cancer Metastasis Rev., 17, 449). Therefore, molecules that act on the actin cytoskeleton of tumor cells and thus inhibit cell division and movement are of high therapeutic value.

In recent years, an increasing number of natural products have been identified that target the actin cytoskeleton and disrupt its organization. Most of them were isolated from marine invertebrate organisms, primarily sponges. All these marine-sponge-derived drugs are unusual macrolides and can be classified into several main families, each with its own distinct chemical structures, biochemical properties, and cellular effects. Among these compounds are lantrunculins (they mimic the activity of monomer sequestering protein, β-thymosins), swinholide A and misakinolide A (they bind to actin monomers and prevent actin filament formation), mycaloide B and aplyronines (both inhibit polymerization of actin), and jasplakinolides (jaspamides), they stabilize actin filaments. Phalloidin is a water soluble bicyclic peptide (FIG. 4a) isolated from the deadly *Amanita phalloides* mushroom one of the class of phallotoxins. It has the same action on actin filaments as jasplakinolides; it binds tightly to actin filaments at nanomolar concentration (Weiland et al., 1977, Curr. Probl. Clin. Biochem., 7, 11; Wehland et al., 1977, Proc. Natl. Acad. Sci. U.S.A, 74, 5613) and stabilizes them against depolymerization, lowering the critical concentration for polymerization up to 30-fold. In contrast to jasplakinolide, which readily enters mammalian cells, phalloidin has not been developed for therapeutic use, since it cannot penetrate the cell membrane itself. Jasplakinolide and other anti-actin drugs penetrate through the membrane of all cells, both normal and cancerous, which significantly reduces their therapeutic effect.

A novel technology of pH-selective translocation of phalloidin through the cell membrane (FIG. 4, 5, 7) is presented. The biological effects of translocation of phalloidin into live cells are expected to be an inhibition of cell contractility and division, together with the formation of multinucleated cells, since nuclei might divide but treated cells cannot. Indeed, the translocation of phalloidin into cells leads to inhibition of cytoskeleton dynamics and consequent loss of the ability of attached cells to contract and round up in response to treatment by EDTA/trypsin dissociation solution (FIG. 11a and FIG. 12).

Figure 11A:
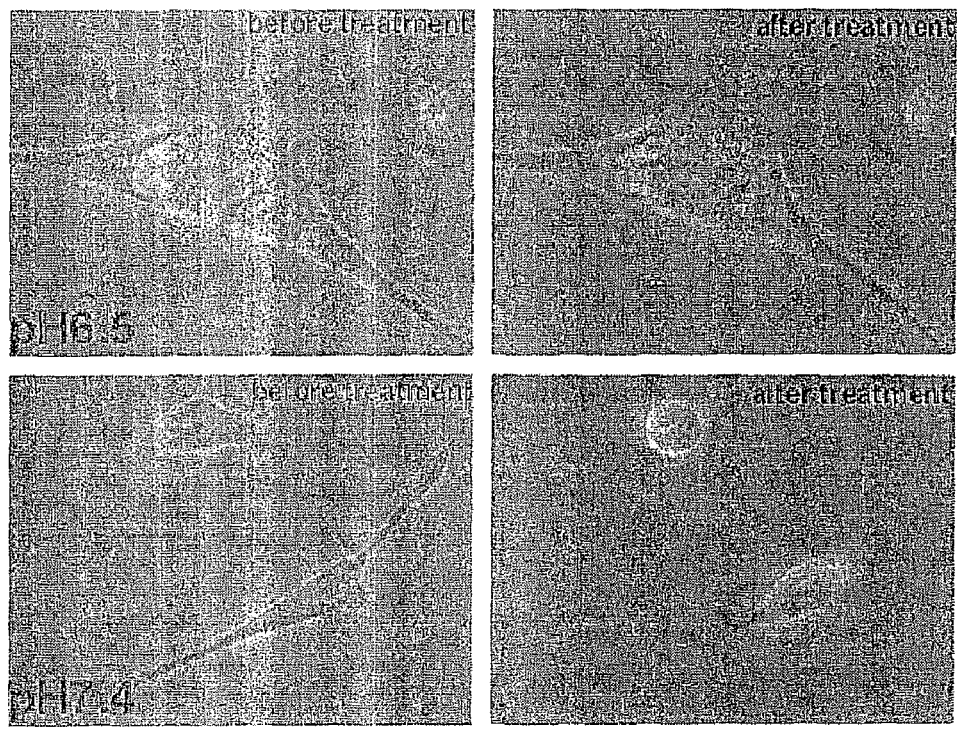
FIG. 11a shows phase-contrast images of HeLa cells incubated (for 1 hour) with a pHLIP-S—S-Phalloidin-TRITC cleavable construct (1 µM) before and after treatment with dissociation solution at various pH's.
Figure 11B:
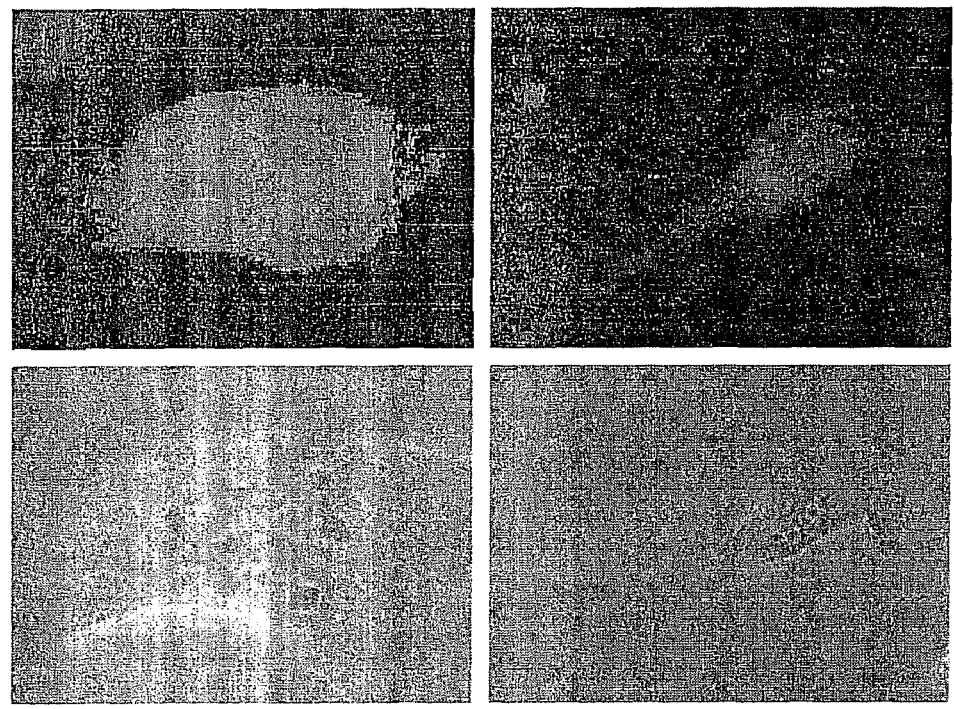
FIG. 11b shows fluorescence images of nuclei stained with 0.5 µM DAPI and corresponding phase contrast images of the multinucleated HeLa cells 48 hours after incubation (1 hour) with a pHLIP-S—S-Phalloidin-TRITC cleavable construct (1 µM)

FIG. 11a illustrates Phase-contrast images of HeLa cells incubated (for 1 hour) with the (1 µM) pHLIP-S—S-Phalloidin-TRITC cleavable construct at pH6.5 and 7.4 followed by washing with PBS pH7.4 before (left) and 5 min after adding of the dissociation solution (right). Cells treated with the peptide-phalloidin at low pH remained unchanged, consistent with stabilization of the cytoskeleton by phalloidin-rhodamine delivered by the pHLIP. FIG. 11b is of fluorescence images of nuclei stained with 0.5 µM DAPI and corresponding phase contrast images of the multinucleated HeLa cells are presented. Multinucleation was observed at 48 hours after treatment of cells with 1 µM of pHLIP-S—S-Phalloidin-TRITC at pH6.5 for 1 hour.

Figure 12:
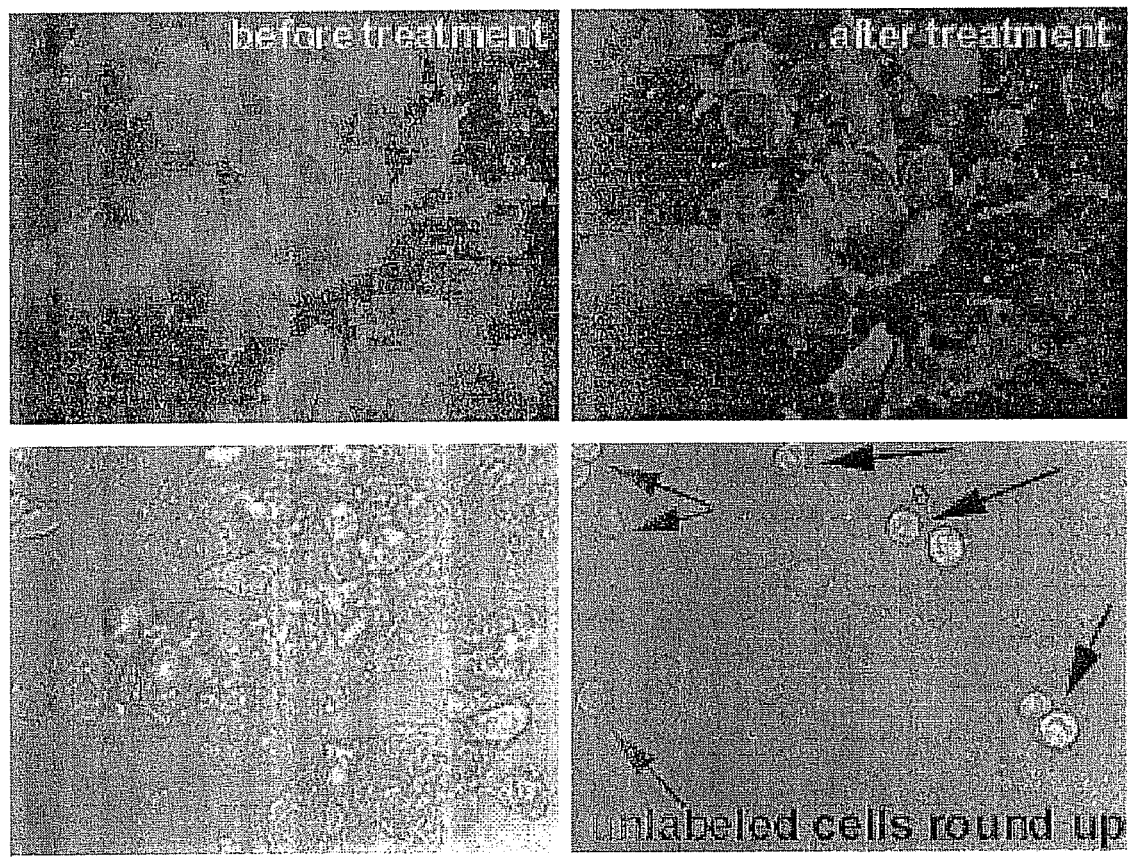
FIG. 12 shows fluorescence and phase-contrast images of the same HeLa cells incubated (for 1 hour) with a pHLIP-S—S-Phalloidin-TRITC cleavable construct (2 µM) were taken before (left) and 5 min after adding of dissociation solution (right)

FIG. 12 is of fluorescence and phase-contrast images of the same HeLa treated with 2 µM of pHLIP-S—S-Phalloidin-TRITC cleavable construct at pH6.5 for 1 hour cells were taken before (left) and 5 min after adding dissociation solution (right). Weakly stained cells became round (arrows) and strongly stained cells remained unchanged, showing the stabilization of the cytoskeleton by phalloidin-rhodamine delivered by the pHLIP.

However, untreated cells or cells treated with the construct at normal pH were able to round up and dissociate from the surface. Also, we observed formation of multinucleated cells after 48 hrs of treatment with pHLIP-S—S-Phalloidin-TRITC (FIG. 11a). The appearance of multinucleated cells (FIG. 11b) has been also reported after treatment of cells with Jasplakinolide.

EXAMPLE 2

Selective Translocation of PNA Through the Cell Membrane by pHLIP

Synthetic molecules that can bind with high sequence specificity to a chosen target in a gene sequence are of major interest in medicinal and biotechnological contexts. They show promise for the development of gene therapeutic agents, diagnostic devices for genetic analysis, and as molecular tools for nucleic acid manipulations. Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen et al., 1991, Science, 254, 1497). It is chemically stable and resistant to hydrolytic (enzymatic) cleavage and thus not expected to be degraded inside a living cell. PNA is capable of sequence-specific recognition of DNA and RNA obeying the Watson-Crick hydrogen bonding scheme, and the hybrid complexes exhibit extraordinary thermal stability and unique ionic strength effects. It may also recognize duplex homopurine sequences of DNA to which it binds by strand invasion, forming a stable PNA-DNA-PNA triplex with a looped-out DNA strand (Ray and Norden, 2000, FASEB J., 14, 1041). Since its discovery, PNA has attracted major attention at the interface of chemistry and biology because of its interesting chemical, physical, and biological properties and its potential to act as an active component for diagnostic as well as pharmaceutical applications. In vitro studies indicate that PNA could inhibit both transcription and translation of genes to which it has been targeted, which holds promise for its use for antigene and antisense therapy. The delivery of synthetic oligodeoxynucleotides (ODN) and oligonucleotides into cells is a major problem in the full development of antisense technology for the control of gene expression in cell culture and in vivo. Even delivery, involving passage through the cell membrane, of PNA, which is much less polar than DNA and RNA, is a major problem.

Figure 13:
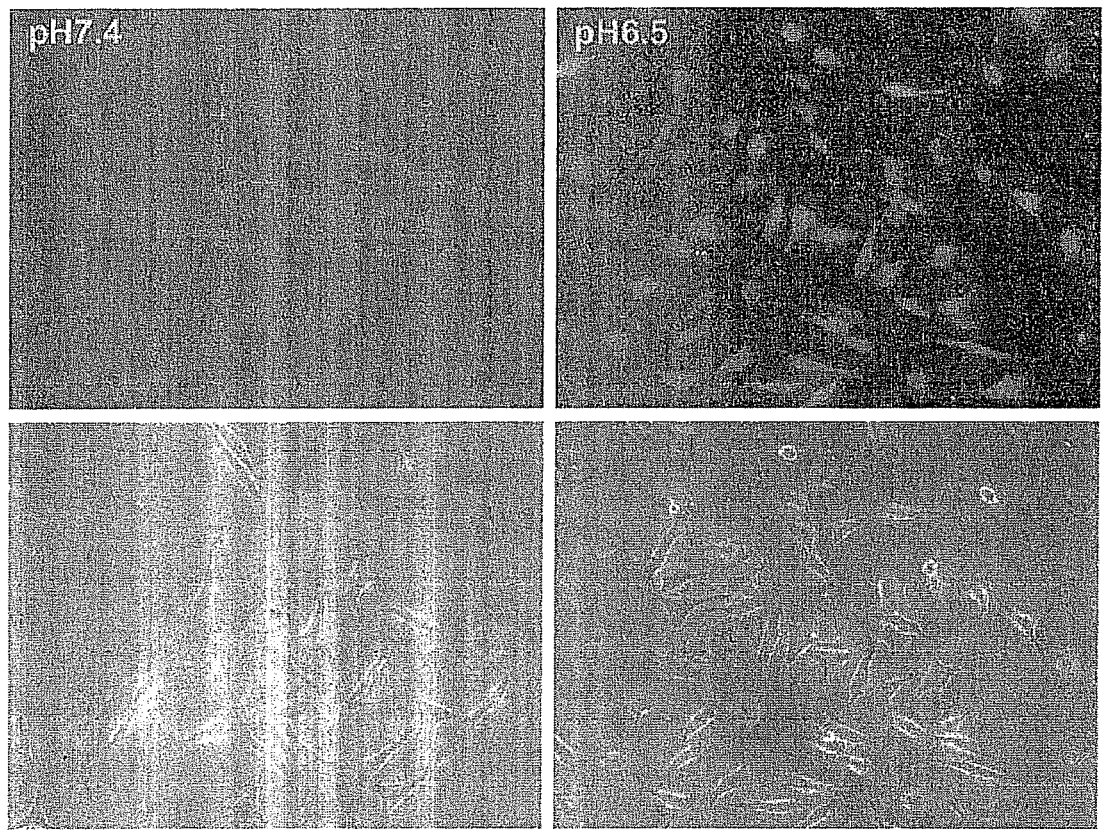
FIG. 13 shows fluorescence and phase-contrast images of HeLa cells treated with 1 µM of a pHLIP-S—S—PNA-TAMRA cleavable construct with the S—S on FSin at pH7.4 and 6.5, showing delivery of the PNA into cells.
Figure 14:
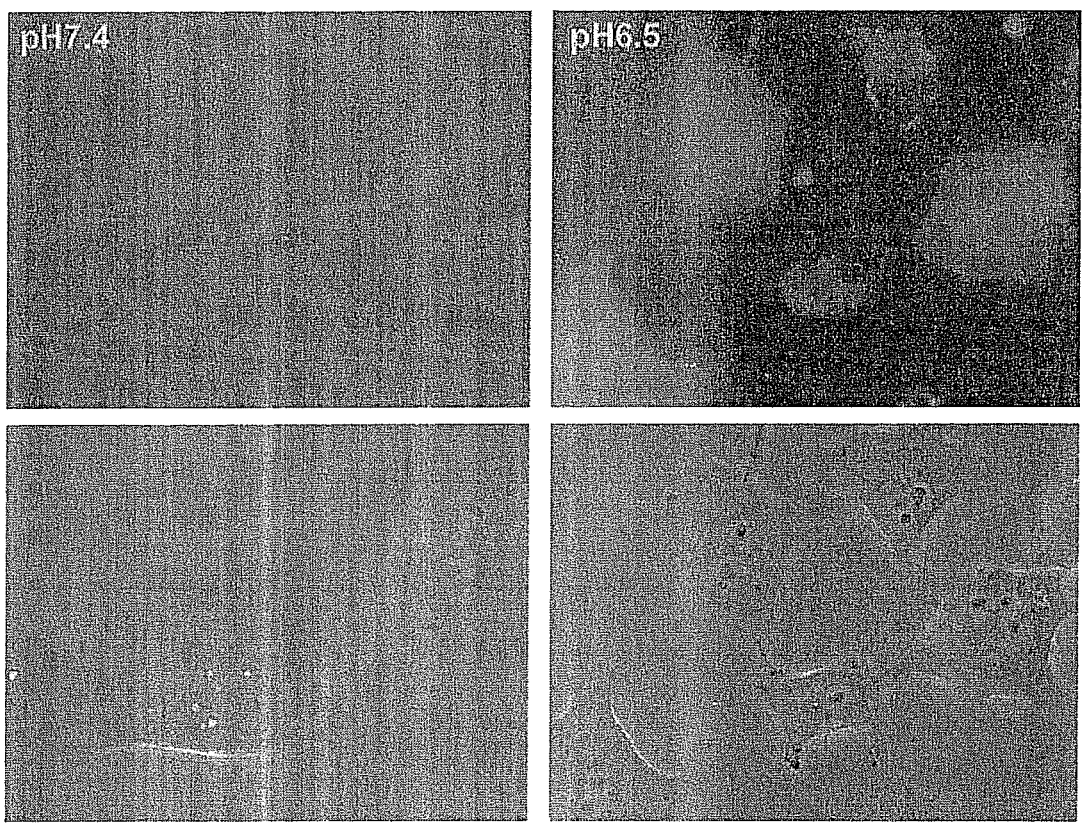
FIG. 14 shows fluorescence and phase-contrast images (100× magnification) of HeLa cells treated with the pHLIP-S—S—PNA-TAMRA cleavable construct (1 µM) at pH7.4 and 6.5.

A novel technology of pH-selective translocation of PNA through the cell membrane is shown in FIGS. 13 and 14. FIG. 13 shows the delivery of PNA into HeLa cells by pHLIP. Fluorescence images of cells incubated (for 30 min) with a pHLIP-S—S-PNA-TAMRA cleavable construct (1 µM) at pH7.4 and 6.5. No translocation was observed of pHLIP-S—S-PNA-TAMRA at pH7.4 or of PNA-TAMRA at either pH7.4 or 6.5 (data not shown). The viability of labeled cells was confirmed using the dead cell marker, SYTOX. The images in FIG. 14 illustrate the delivery of PNA into HeLa cells by pHLIP. Fluorescence images at magnification 100× of cells incubated with a pHLIP-S—S-PNA-TAMRA cleavable construct at pH7.4 and 6.5. No translocation was observed of pHLIP-S—S-PNA-TAMRA at pH7.4. However, pHLIP translocated PNA through the cell membrane at pH6.5.

The efficiency of translocation of fluorescently labeled PNA by pHLIP was high at low pH (6.5) and practically zero at normal pH.

There are many diseases which create low extracellular pH and therefore the peptide is expected to be functional. Hypoxia and acidosis are physiological markers of many diseased processes such as a cancer (Stubbs et al., 2000, Mol. Med. Today, 6, 15; Helmlinger et al., 2002, Clin. Cancer Res. 8, 1284; Izumi et al. 2003, Cancer Treat. Reviews. 29, 541); an infarction (Graham et al., 2004, J Exp Biol., 207, 3189; Yao and Haddad, 2004, Cell Calcium., 36, 247; Yamamoto and Ehara, 2005, Am J Physiol Heart Circ Physiol., in press); a stroke (Rehncrona 1985, Ann. Emerg. Med. 14, 770; Siesjo et al., 1996, Adv. Neurol. 71, 209; Ying et al., 1999, J. Neurochem. 73, 1549); an atherosclerotic lesion (Leake 1997, Atherosclerosis, 129, 149); a trauma (Mikhail, 1999, AACN Clin Issues, 10, 85; Clausen et al., 2005, J Neurosurg, 103, 597); an inflammation (Kalantar-Zadeh et al., 2004, Semin Dial, 17, 455); an infection (Holloway et al., 1995; Exp Parasitol., 80, 624; Headley, 2003, Am Fam Physician., 68, 323).

It will be apparent to those skilled in the art that the present invention may be embodied in may other specific forms without departing from the spirit or scope of the invention. Therefore, the present embodiment is to be considered as illustrative and not restrictive and the invention is not to be limited to the details given herein, but may be modified within the scope of the appended claims.

What is claimed is:

1. A purified peptide comprising SEQ ID NO:1.

2. A conjugate comprising a compound covalently bound to an amino-terminal residue or a carboxy-terminal residue of a peptide comprising SEQ ID NO:1, wherein said compound comprises a therapeutic, diagnostic, prophylactic, imaging, gene regulation, cell function regulation, or apoptotic compound.

3. The conjugate of claim 2, wherein said therapeutic compound comprises a cytotoxic molecule.

4. The conjugate of claim 2, wherein said diagnostic compound comprises a fluorescent molecule.

5. The peptide of claim 1, wherein said peptide further comprises a Cys residue at the amino-terminus of SEQ ID NO:1.

6. A conjugate comprising a compound covalently bound to the Cys residue of the peptide of claim 1, wherein said compound comprises a therapeutic, diagnostic, imaging, gene regulation, cell function regulation, or apoptotic compound.

7. A conjugate comprising a compound covalently bound to the Cys residue at the amino terminus of the peptide of claim 5, wherein said compound comprises a therapeutic, diagnostic, imaging, gene regulation, cell function regulation, or apoptotic compound.

8. The conjugate of claim 6, wherein said therapeutic compound comprises a cytotoxic molecule.

9. The conjugate of claim 6, wherein said diagnostic compound comprises a fluorescent molecule.

10. The conjugate of claim 7, wherein said therapeutic compound comprises a cytotoxic molecule.

11. The conjugate of claim 7, wherein said diagnostic compound comprises a fluorescent molecule.

12. A peptide in which one or more L-amino acids in SEQ ID NO:1 is substituted with a corresponding D-isomer.

13. The peptide claim 1 or 5, wherein said peptide comprises L-amino acids.

14. The peptide claim 6 or 7, wherein said peptide comprises L-amino acids.

15. A peptide comprising SEQ ID NO:1 and further comprising a Cys residue at the amino-terminus of SEQ ID NO:1, wherein one or more L-amino acids in the peptide is substituted with a corresponding D-isomer.

16. A conjugate comprising a compound covalently bound to the Cys residue of SEQ ID NO:1, wherein said compound comprises a therapeutic, diagnostic, imaging, gene regulation, cell function regulation, or apoptotic compound and wherein one or more L-amino acids in SEQ ID NO:1 is substituted with a corresponding D-isomer.

17. A conjugate comprising the peptide of claim 15 and a compound covalently bound to the Cys residue at the amino-terminus of the peptide, wherein said compound comprises a therapeutic, diagnostic, imaging, gene regulation, cell function regulation, or apoptotic compound.

* * * * *

UNITED STATES PATENT AND TRADEMARK OFFICE
CERTIFICATE OF CORRECTION

| | | |
|---|---|---|
| PATENT NO. | : 8,076,451 B2 | Page 1 of 1 |
| APPLICATION NO. | : 11/778323 | |
| DATED | : December 13, 2011 | |
| INVENTOR(S) | : Yana K. Reshetnyak et al. | |

It is certified that error appears in the above-identified patent and that said Letters Patent is hereby corrected as shown below:

In the Specification:

At column 1, line numbers 19-22, the paragraph "The United States government has rights in this invention by virtue of grant number GM 054160 from the National Institute of Health and 9905671 from the National Science Foundation" should read --The United States government has rights in this invention by virtue of grant number GM 054160 from the National Institutes of Health, 9905671 from the National Science Foundation, and Grant No. W81XWH-06-0306 from the United States Army.--

Signed and Sealed this
Thirteenth Day of March, 2012

David J. Kappos
*Director of the United States Patent and Trademark Office*

UNITED STATES PATENT AND TRADEMARK OFFICE
CERTIFICATE OF CORRECTION

Page 1 of 1

PATENT NO.         : 8,076,451 B2
APPLICATION NO.    : 11/778323
DATED              : December 13, 2011
INVENTOR(S)        : Yana K. Reshetnyak et al.

It is certified that error appears in the above-identified patent and that said Letters Patent is hereby corrected as shown below:

In the Specification:

At column 1, line numbers 19-22, the paragraph "The United States government has rights in this invention by virtue of grant number GM 054160 from the National Institutes of Health, 9905671 from the National Science Foundation, and Grant No. W81XWH-06-0306 from the United States Army" should read -- "This invention was made with government support under Grant No. GM 054160 awarded by National Institutes of Health, Grant No. 9905671 awarded by National Science Foundation, and Grant No. W81XWH-06-1-0306 awarded by the United States Army. The government has certain rights in the invention." --

This certificate supersedes the Certificate of Correction issued March 13, 2012.

Signed and Sealed this
Eleventh Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 8,076,451 B2
APPLICATION NO. : 11/778323
DATED : December 13, 2011
INVENTOR(S) : Yana K. Reshetnyak et al.

It is certified that error appears in the above-identified patent and that said Letters Patent is hereby corrected as shown below:

In the Specification

At Column 1, Line numbers 19-22, the paragraph "This invention was made with government support under Grant No. GM 054160 awarded by National Institutes of Health, Grant No. 9905671 awarded by National Science Foundation, and Grant No. W81XWH-06-1-0306 awarded by the United States Army. The government has certain rights in the invention" should read -- "This invention was made with government support under GM054160 awarded by the National Institutes of Health, 9905671 awarded by the National Science Foundation and W81XWH-06-1-0306 awarded by the ARMY/MRMC. The government has certain rights in the invention." --

This certificate supersedes the Certificate of Correction issued August 11, 2015.

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 2

<210> SEQ ID NO 1
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Glu Gln Asn Pro Ile Tyr Trp Ala Arg Tyr Ala Asp Trp Leu
 1               5                  10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catagtataa gt                                                         12
```